United States Patent [19]

Moussa et al.

[11] Patent Number: 6,086,376

[45] Date of Patent: Jul. 11, 2000

[54] DRY AEROSOL SUSPENSION OF PHOSPHOLIPID-STABILIZED DRUG MICROPARTICLES IN A HYDROFLUOROALKANE PROPELLANT

[75] Inventors: Iskandar Moussa, Montreal; Indu Parikh, Verdun, both of Canada

[73] Assignee: RTP Pharma Inc., Quebec, Canada

[21] Appl. No.: 09/016,265

[22] Filed: Jan. 30, 1998

[51] Int. Cl.[7] ............................. A61L 9/04; A61K 9/127
[52] U.S. Cl. ................................................ 434/45; 424/450
[58] Field of Search ................................ 424/45, 46, 450

[56] References Cited

U.S. PATENT DOCUMENTS

| | | |
|---|---|---|
| 4,174,295 | 11/1979 | Bargigia et al. . |
| 5,118,494 | 6/1992 | Schultz et al. . |
| 5,126,123 | 6/1992 | Johnson . |
| 5,145,684 | 9/1992 | Liversidge et al. ................ 424/489 |
| 5,182,097 | 1/1993 | Byron et al. . |
| 5,202,110 | 4/1993 | Dalby et al. . |
| 5,225,183 | 7/1993 | Purewal et al. ................ 424/45 |
| 5,474,759 | 12/1995 | Fassberg et al. . |
| 5,492,688 | 2/1996 | Byron et al. . |
| 5,552,160 | 9/1996 | Liversidge et al. ................ 424/489 |
| 5,653,962 | 8/1997 | Akehurst et al. ................ 424/45 |
| 5,674,471 | 10/1997 | Akehurst et al. ................ 424/45 |

FOREIGN PATENT DOCUMENTS

| | | |
|---|---|---|
| 0 535 567 | 4/1993 | European Pat. Off. . |
| 0 634 166 | 1/1995 | European Pat. Off. . |
| 90/11754 | 10/1990 | WIPO . |
| 91/04011 | 4/1991 | WIPO . |
| 91/11495 | 8/1991 | WIPO . |
| 92/06675 | 4/1992 | WIPO . |
| 93/05765 | 4/1993 | WIPO . |
| 91/11745 | 6/1993 | WIPO . |
| 93/11743 | 6/1993 | WIPO . |
| 93/11744 | 6/1993 | WIPO . |
| 93/15741 | 8/1993 | WIPO . |
| 94/03153 | 2/1994 | WIPO . |
| 94/21228 | 9/1994 | WIPO . |
| 96/06598 | 3/1996 | WIPO . |
| 96/18384 | 6/1996 | WIPO . |
| 96/19197 | 6/1996 | WIPO . |
| 96/19198 | 6/1996 | WIPO . |
| 96/32099 | 10/1996 | WIPO . |
| 96/32150 | 10/1996 | WIPO . |
| 96/32151 | 10/1996 | WIPO . |
| 96/40089 | 12/1996 | WIPO . |
| 97/44012 | 11/1997 | WIPO . |

*Primary Examiner*—Thurman K. Page
*Assistant Examiner*—Susan Tran
*Attorney, Agent, or Firm*—Nixon & Vanderhye

[57] ABSTRACT

Aerosol formulations containing stabilized particles of drug microparticles with a mean size range of 0.1 to 10 microns coated with a membrane-forming, amphiphatic lipid and dispersed in 1,1,1,2-tetaafluoroetiane (HFA 134a) of 1,1,1,2,3,3,3-heptafluoropropane (HFA 227) propellant.

16 Claims, No Drawings

DRY AEROSOL SUSPENSION OF PHOSPHOLIPID-STABILIZED DRUG MICROPARTICLES IN A HYDROFLUOROALKANE PROPELLANT

This invention relates to aerosol formulations of drug microparticles coated with a lipid membrane and suspended in a hydrofluoroalkane propellant, as a dry powder or in a pharmaceutically acceptable carrier.

BACKGROUND OF THE INVENTION

The delivery of drugs in pressurized metered-dose inhalers (MDI) currently employs the chlorofluorocarbons as propellants. As a result of the phase out of chlorofluorocarbons (potential depletion of the ozone layer), products marketed using chlorofluorocarbons must be reformulated using hydrofluoroalkane (HFA) propellants e.g 1,1,1,2-tetrafluoroethane (HFA 134a) and 1,1,1,2,3,3,3-heptafluoropropane (HFA 227), marketed by Du Pont Chemicals, Wilmington, Del., USA. The solvent behavior of the proposed alternative propellants is quite different from that of the chlorofluorocarbons. Difference in the physicochemical properties, such as polarity, vapor pressure and density, has posed challenges to the development of drug products in pressurized metered-dose inhalers for pulmonary delivery using hydrofluoroalkanes as propellants [Byron et al., Resp. Drug Deliv., 4 (1994)].

Numerous patent documents address these differences in physiochemical properties in formulations for inhalation. U.S. Pat. No. 5,492,688 relates to MDI formulations which utilize greater than 90% by weight of HFA 134a as the sole propellant, less than 5% w/w of micronized drug particles and less than 5% w/w of a polar surfactant selected from the group consisting of polyethylene glycol 300, diethylene glycol monoethyl ether, polyoxyethylene 20 sorbitan monooleate, propoxylated polyethylene glycol, and polyoxyethylene 4 lauryl ether.

World patent WO 91/04011 describes a self-propelling powder aerosol composition containing finely-divided, pre-micronized solid drug coated with a single non-perfluorinated surface-active dispersing agent suspended in an aerosol propellant in which the dispersing agent is substantially insoluble. Suitable dispersing agents include various oils, sorbitan oleates, polyoxyethylene sorbitans, lecithins and polyoxyethylene among others. The quantity of surfactant used is kept to a minimum to avoid particle agglomeration and increase particle size.

World patent application 96/19197 relates to a pharmaceutical aerosol formulation comprising (a) a hydrofluoroalkane propellant; (b) a pharmaceutically active polypeptide dispersible in the propellant; and (c) a surfactant which is a C8–C16 fatty acid or salt thereof, a bile salt, a phospholipid, or an alkyl saccharide, which surfactant enhances the systemic absorption of the polypeptide in the lower respiratory tract. World patent application 96/19198 by the same inventors relates to a pharmaceutical aerosol formulation comprising a HFA propellant; a physiologically effective amount of a medicament for inhalation; and a surfactant which is a C8–C16 fatty acid or salt thereof, a bile salt, a phospholipid, or an alkyl saccharide. Both patents describe physical mixtures of active and surfactant in the propellant, with no prior encapsulation steps involved.

World patent application 96/40089 relates to a pharmaceutical aerosol formulation a pharmaceutical composition for aerosol delivery containing a medicament, a halogenated alkane propellant, and a biocompatible C16+-unsaturated vegetable oil.

World patent application 90/11754 relates to an aerosol formulation containing, as active ingredient, an azole antifungal in a form suitable for administration by inhalation.

World patent application 94/21228 relates to a medicinal aerosol formulation having a diol/diacid condensate as a dispersing agent, a propellant, and a therapeutically effective amount of a particulate drug.

World patent application 96/06598 relates to a pharmaceutical composition for aerosol delivery comprising a medicament, a non-chlorofluorocarbon propellant, and a polyglycolyzed glyceride.

World patent application 92/06675 relates to an aerosol formulation containing a therapeutically effective amount of beclomethasone 17,21 diproprionate, hydrofluorocarbon 1,1,1,2-tetrafluoroethane (HFA 134a) or 1,1,1,2,3,3,3-heptafluoropropane (HFA 227) propellant or a mixture and ethanol in an amount effective to solubilize the beclomethasone 17,21 diproprionate in the propellant. Substantially all the beclomethasone 17,21 diproprionate is dissolved in the formulation, and it is substantially free of any surfactant.

World patent application 93/05765 relates to a pressurized aerosol composition comprising a liquefied hydrofluoroalkane, a powdered medicament dispersible therein and a polymer soluble in the liquefied hydrofluoroalkane. The polymer includes, amide containing units or carboxylic acid ester containing units as recurring structural units.

U.S. Pat. No. 4,174,295 relates to a propellant composition for use with aerosols, the composition consisting essentially of a mixture of from 5 to 60% by weight, based on the total weight of the propellant composition, of a hydrogen-containing fluorocarbon selected from $CH_2F_2$ and $CF_3$—$CH_3$, and from 40 to 95% by weight, based on the total weight of the propellant composition, of a hydrogen-containing chlorofluorocarbon or a hydrogen-containing fluorocarbon, each selected from $CF_3$—$CHClF$, $CF_3$—$CH_2Cl$, $CF_3$—$CH_2F$, $CClF_2$—$CF_3$ or $CHF_2$—$CH_3$.

U.S. Pat. No. 5,118,494 relates to a suspension aerosol formulation, including: a propellant comprising a hydrofluorocarbon selected from 1,1,1,2-tetrafluoroethane (HFA 134a) or 1,1,1,2,3,3,3-heptafluoropropane (HFA227), or a mixture, a therapeutically effective amount of a powdered medicament; and between about 0.001 and 0.6% by weight based on the total weight of the formulation of a perfluorinated carboxylic acid or ester as surface-active dispersing agent. The formulation exhibits substantially no crystallization of medicament over a prolonged period, is readily redispersible, and upon redispersion non flocculating so quickly as to prevent reproducible dosing of the medicament.

U.S. Pat. No. 5,126,123 relates to an aerosol inhalation drug formulation consisting essentially of a physiologically effective amount of a micronized inhalation drug and a 1,1,1,2-tetrafluoroethane-soluble, perfluoronated surfactant in suspension in 1,1,1,2-tetrafluoroethane.

U.S. Pat. No. 5,182,097 relates to an aerosol formulation for use in delivering medication to a patient via an inhalation device, comprising a propellant consisting solely of 1,1,1,2-tetrafluoroethane. The propellant represents at least 90% by weight of the aerosol formulation; an inhalable medicament dispersed or dissolved in a propellant, an inhalable medicament having a partition size less than 100 microns in diameter. The inhalable medicament represents no more than 5% by weight of aerosol formulation. Oleic acid employed as a surfactant for aiding in dispersing the inhalable medicant in the propellant, with oleic acid no more than 0.2% w/v of aerosol formulation.

U.S. Pat. No. 5,202,110 relates to an aerosol formulation for use in a metered dose inhaler, comprising a pharmaceutically acceptable inhalable propellant; a clathrate or molecular association of beclomethasone diproprionate employed as inhalable medicant dispersed or dissolved in a propellant. The clathrate or molecular association of beclomethasone diproprionate is formed with 1,1-dichloro-2,2,2-trifluoroethane, or 1,1-dichloro-1-fluoroethane, or dimethyl ether; the clathrate or molecular association having a particle size permitting inhalation.

U.S. Pat. No. 5,474,759 relates to an aerosol formulation consisting essentially of an effective amount of medicament; 1,1,1,2,3,3,3-heptafluoropropane (HFA 227); optionally, an excipient selected from a propylene glycol diester of a medium chain fatty acid or a triglyceride ester of a medium chain fatty acid. A surfactant is optionally present together with other excipients.

World patent application 96/32150 relates to a metered dose having, part or all of its internal surfaces coated with one or more fluorocarbon polymers, optionally in combination with one or more non-fluorocarbon polymers, for dispensing an inhalation drug formulation of salmeterol, or a physiologically acceptable salt thereof, and a fluorocarbon propellant, optionally in combination with one or more other pharmacologically active agents or one or more excipients.

World patent application 96/32151 relates to a metered dose inhaler having part or all of its internal surfaces coated with one or more fluorocarbon polymers, optionally in combination with one or more non-fluorocarbon polymers, for dispensing an inhalation drug formulation of fluticasone propionate, or a physiologically acceptable solvate thereof, and a fluorocarbon propellant, optionally in combination with one or more other pharmacologically active agents or one or more excipients.

World patent application 96/18384 relates to a pharmaceutical aerosol formulation of 1,1,1,2-tetrafluoroethane (HFA 134a), 1,1,1,2,3,3,3-heptafluoropropane (HFA 227) or mixtures thereof as propellant; 1,1,2,2,3-pentafluoropropane as co-propellant; and particulate medicament.

World patent application 94/03153 relates to a pharmaceutical aerosol formulation of particulate beclomethasone diproprionate or an acceptable solvate together with a fluorocarbon or hydrogen-containing chlorofluorocarbon propellant, which formulation is substantially free of surfactant.

World patent application 96/32099 relates to a metered dose inhaler having part or all of its internal surfaces coated with one or more fluorocarbon polymers, optionally in combination with one or more non-fluorocarbon polymers, for dispensing an inhalation drug formulation of albuterol, or a physiologically acceptable salt thereof, and a fluorocarbon propellant, optionally in combination with one or more other pharmacologically active agents or one or more excipients.

World patent application 93/11745 relates to a pharmaceutical aerosol formulation of a particulate medicament, a fluorocarbon or hydrogen-containing chlorofluorocarbon propellant and up to 5% w/w based upon propellant of a polar cosolvent, which formulation is substantially free of surfactant.

World patent application 93/11743 relates to a pharmaceutical aerosol formulation comprising particulate medicament of salmeterol, salbutamol, fluticasone propionate, beclomethasone dipropionate or their physiologically acceptable salts and solvates, and a fluorocarbon or hydrogen-containing chlorofluorocarbon. The formulation is substantially free of surfactant.

World patent application 93/15741 relates to a pharmaceutical aerosol formulation of beclomethasone dipropionate monohydrate, the particle size of substantially all the monohydrate being less than 20 microns; at least 0.015% w/w of the formulation of water in addition to the water of crystallization associated with the monohydrate; and a fluorocarbon or hydrogen-containing chlorofluorocarbon propellant.

World patent application 93/11744 relates to pharmaceutical aerosol formulation of a particulate medicament and a fluorocarbon or hydrogen-containing chlorofluorocarbon propellant, the formulation is substantially free of surfactant and when the medicament is other than salmeterol, salbutamol, fluticasone propionate, beclomethasone dipropionate or physiologically acceptable salts or solvate thereof.

SUMMARY OF THE INVENTION

In accordance with the present invention it has now surprisingly been found that particularly stable suspensions of microparticles in HFA 134a or HFA 227 are obtainable. These microparticles consist of drug microparticles coated with a phospholipid containing membrane. Preferably the drug particles are coated with a mixture of phospholipid(s) and at least one surfactant forming a membrane layer enveloping the outside of the microparticles. The mean particle size of the drug is reduced to between 100 nm to 10 microns, preferably 0.1 to 10 microns, by sonication or other processes inducing high shear and/or impaction in the presence of phosphlolipids or other membrane-forming amphiphatic lipids and, preferably, at least one surfactant. Dry powder is then obtained by drying the suspension. The dry powder of coated particles is conveniently suspended in the propellant. The membrane forming ingredients are used to obtain appropriate densities and polarities and decreased drug particle-coalescence, thus leading to well dispersible and stable drug suspensions in the hydrofluorocarbon propellants HFA 134a or HFA 227.

DESCRIPTION OF INVENTION

In a preferred aspect of the invention drug particles are coated with mixtures of phospholipids and at least one surfactant with simultaneous size reduction to give a resultant mean particle size of 0.1 to 10 microns. These excipients are used in order to adjust the density, the polarity and the surface tension of the drug particles suspended in the propellant. Control of the density reduces the tendency of dispersed particles to either cream or sediment. The density of the formulation is preferred to be in the range of 1.0 to 1.5 g/ml so as to match with the density of the HFA propellants. Also, appropriate control of the polarity and surface tension of the particles decrease drug-particle coalescence and to yields easily dispersible and stable drug suspensions.

In the membrane coating the weight ratio of phospholipid (s) to surfactant(s) is in the range of 0.01 to 100, preferably in the range of 0.02 to 50 and more preferably in the range of 0.04 to 25. The type and amount of surfactant and cosurfactant used is based on the relative solubility and/or polarity of these ingredients. The formulation compositions are hence optimized with respect to each drug individually. The encapsulation process minimizes the amounts of excipients needed to obtain acceptable formulations.

Importantly, the total amount of surface active agents, including phospholipids, is preferably more than 0.1% and less than 200% of the drug content.

DETAILED DESCRIPTION OF THE INVENTION

Methods of preparation

Sonication method: The sonication process reduces the size of supra-molecular drug and phospholipid structures by the process of cavitation. The process creates small empty volumes that collapse, propelling material together at high speed, resulting in shattering and sheer. This allows one to simultaneously break up the ingredients into submicron fragments and coat the hydrophobic surface of microparticle. In the current invention the sonication process is used after the drug, the phospholipid(s), the surfactant(s) and any additional ingredient(s) are mixed together with a solvent. Sonication is performed at controlled temperature of between 5–10° C. with sonic dismembrator model 550 (Fisher Scientific) fitted with 0.5 inch probe at a power setting of 3–5 for 5 to 60 min until the mean particle size reaches between 0.1–5 microns. In order to better control the temperature, sonication is performed with automated 10 seconds on and 10 seconds off cycle.

The product is then converted into dry form by lyophilization or spray drying to yield a powder which is then suspended in HFA 134a or HFA 227.

Methods involving high pressure causing high shear and impaction: The drug together with other appropriate ingredients are homogenized by high pressure homogenization and/or microfluidization as known in the art. In the microfluidization process, high shear is created by collision of opposing microjets of liquids and impaction occurs between particle and at walls of the fluidizer. In the high pressure homogenization process, the sample is forced at high pressure and high shear through a narrow orifice and undergoes impaction against a wall and rapid decompression to atmospheric pressure. The product is then converted into dry form by lyophilization or spray drying to yield a powder which is then suspended in HFA 134a or HFA 227. Sonication and high shear and impaction methods are not limited to aqueous media but also may be performed in volatile organic solvents.

Size reduction in air: Drug crystals can also be reduced in size by high speed impact in air and then subsequently coated by phospholipid and surfactants. The product is then converted into dry form by lyophilization or spray drying to yield a powder which is then suspended in HFA 134a or HFA 227.

Size reduction by in-flight crystallization: A solution of the phospholipid(s), surfactant(s), the drug and any additional ingredient in a volatile solvent can be sprayed, with simultaneous removal of solvent by evaporation while in flight. The dried particles are collected on a smooth surface and suspended in one of the propellants.

Size reduction by controlled crystallization methods: such as crystallization using supercritical fluids.

Compositions of the current invention will include, in addition to the active, at least one phospholipid and optionally at least one surfactant.

Examples of suitable phospholipids are: diacylphosphatidylcholine in saturated or unsaturated form; diacylphosphatidylglycerols, diacylphosphatidylethanolamines, diacylphosphatidylinositols and diacylphosphatidylserines in saturated or unsaturated form and the corresponding lysophospholipids.

Examples of suitable surfactants are:

1. Polyoxyethylene-sorbitan-fatty acid esters; e.g. mono- and tri-lauryl, palmityl, stearyl and oleyl esters; e.g. products of the type known as polysorbates and commercially available under the trade name "Tween".
2. Polyoxyethylene fatty acid esters, e.g., polyoxyethylene stearic acid esters of the type known and commercially available under the trade name Myrj, such as Myrj 52.
3. Polyoxethylene castor oil derivatives, e.g., products of the type known and commercially available as Cremophors. Particularly suitable are polyoxyl 35 castor oil (Cremophor EL) and polyoxyl 40 hydrogenated castor oil (Cremophor RH40).
4. Vitamin E or its derivatives, such as D-a-tocopheryl polyethylene glycol 1000 succinate (vitamin E TPGS).
5. PEG glyceryl fatty acid esters such as PEG-8 glyceryl caprylate/caprate (commercially known as Labrasol), PEG-4 glyceryl caprylate/caprate (Labrafac Hydro WL 1219), PEG-32 glyceryl laurate (Gelucire 44/14),), PEG-6 glyceryl mono oleate (Labrafil M 1944 CS), PEG-6 glyceryl linoleate (Labrafil M 2125 CS),
6. Propylene glycol mono- and di-fatty acid esters, such as propylene glycol laurate, propylene glycol caprylate/caprate; also diethylene glycol monoethyl ether, commercially known as transcutol.
7. Sorbitan fatty acid esters, such as the type known and commercially available under the trade name Span (e.g., Span 20).
8. Polyoxyethylene-polyoxypropylene co-polymers, e.g., products of the type known and commercially available as Pluronic or Poloxamer, such as Poloxamer 188 NF.
9. Glycerol triacetate
10. Monoglycerides and acetylated monoglycerides, e.g., glycerol monooleate, glycerol monostearate and mono- and di-acetylated monoglycerides.
11. Bile salts
12. Polyethylene glycol (PEG); e.g. PEG 300, PEG 400, PEG 600, PEG 1000, PEG 1500, PEG 3400; such as the type known and commercially available under the trade name Carbowax, Lutrol E and Hodag PEG.
13. Substituted cellulose products such as hydroxypropylmethylcellulose, sodium carboxymethyl cellulose and hydroxypropylcellulose.
14. Carbomers, such as the type known and commercially available under the trade name Carbopol.

Suitable phospolipids and surfactants are not limited to those mentioned above, but may include any compound that would enhance the galenic properties of the formulations.

Compositions in accordance with the present invention may include other ingredients in addition to the drug, the phospholipid(s) and the surfactant(s). For example, the composition may include, in addition to the forgoing, one or more ingredients, additives or diluents such as pharmaceutically acceptable or inorganic materials, cryoprotectants such as trehalose and mannitol, anti-oxidants and preserving agents.

The aerosol formulation of the present invention is useful for the local or systemic treatment of diseases and may be administered for example topically or via the upper and lower respiratory tract, including by nasal route.

The following are illustrative but non limiting examples of compositions in accordance with the present invention.

In the following examples, microparticle formulations (30 ml scale) were prepared by addition of the ingredients into the appropriate solvent followed by sonication. The solvent was then evaporated, using e.g. lyophilization.

Appropriate amounts of the dry powder were then weighed and placed into aerosol bottles followed by the addition about 40 ml of HFA 134a per bottle. Bottles were then shaken by hand for about 1 min., sonicated for 15–30 min in a water bath sonicator and/or on a shaker overnight.

| Component | Wt % |
|---|---|
| Example 1 | |
| Beclomethasone dipropionate | 0.0657 |
| DPPC[1] | 0.0263 |
| Myrj 52 | 0.0263 |
| HFA 134a | 99.882 |
| Example 2 | |
| Beclomethasone dipropionate | 0.327 |
| DPPC | 0.177 |
| DMPG[2] | 0.0026 |
| Poloxamer 188 NF | 0.0654 |
| HFA 134a | 99.428 |
| Example 3 | |
| Beclomethasone dipropionate | 0.0657 |
| DPPC | 0.0131 |
| Poloxamer 188 NF | 0.0066 |
| PEG 300 | 0.0066 |
| HFA 134a | 99.908 |
| Example 4 | |
| Flunisolide | 0.3274 |
| DPPC | 0.0655 |
| Poloxamer 188 NF | 0.0524 |
| PEG 1000 | 0.0131 |
| HFA 134a | 99.542 |
| Example 5 | |
| Triamcinolone acetonide | 0.2622 |
| DPPC | 0.0524 |
| Poloxamer 188 NF | 0.0420 |
| PEG 1000 | 0.0105 |
| HFA 134a | 99.633 |
| Example 6 | |
| Salbutamol | 0.1313 |
| DPPC | 0.0368 |
| Myrj 52 | 0.0263 |
| HFA 134a | 99.806 |

[1]1,2-Dipalmitoyl-phosphatidylcholine
[2]1,2-Dimyristoyl-phosphatidylglycerol

What is claimed is:

1. A dry suspension aerosol formulation having a density in the range of from 1.0 to 1.5 g/ml consisting essentially of stabilized drug microcrystals in a mean size range of 0.1 to 10 microns as a core coated with an envelope of one or more membrane-forming phospholipids and at least one surfactant surrounding the drug core and dispersed in 1,1,1,2-tetrafluoroethane HFA134a or 1,1,1,2,3,3,3-heptafluoropropane HFA227 propellant, wherein the density of the coated drug microparticles substantially matches the density of the propellant and the amount of phospholipid coating on the drug microparticles is more than 0.1% and less than 200% of the weight of the drug.

2. The aerosol formulation of claim 1 in which the phospholipid coating also includes at least one surfactant.

3. The aerosol formulation of claim 1 in which the propellant represents at least 70% by weight of the formulation.

4. The aerosol formulation of claim 3 in which the propellant represents at least 90% by weight of the formulation.

5. The aerosol formulation of claim 3 in which the drug represents less than 5% by weight of the formulation.

6. The aerosol formulation of claim 1 in which the weight ratio of phospholipid to surfactant is in the range of 0.04 to 25.

7. The aerosol formulation of claim 1 in which the weight ratio of phospholipid to surfactant is in the range of 0.02 to 50.

8. The aerosol formulation of claim 1 in which the ratio of phospholipids to surfactants is in the range of 0.01 to 100.

9. The aerosol formulation of claim 1 in which the phospholipid represents less than 20% by weight of the formulation.

10. The aerosol formulation of claim 1 in which the phospholipid represents less than 5% by weight of the formulation.

11. The aerosol formulation of claim 1 in which the surfactant represents less than 20% by weight of the formulation.

12. The aerosol formulation of claim 1 in which the surfactant represents less than 5% by weight of the formulation.

13. A metered dose inhaler containing an aerosol formulation having a density ranging from 1.0 to 1.5 g/ml consisting essentially of drug microparticles having a mean size range of 0.1 to 10 microns, coated with a mixture of phospholipids and at least one surfactant, the microparticles dispersed in HFA 134a or HFA 227 propellant, wherein the density of the coated drug microcrystals substantially matches the density of the propellant and the amount of coating on the drug microparticles is no more than 0.1% and less than 200% of the weight of the drug.

14. The aerosol formulation of claim 8 in which the ratio of phospholipids to surfactants is in the range of 0.04 to 25.

15. Drug microparticles having a density in the range of from 1.0 to 1.5 g/ml consisting essentially of stabilized drug microcrystals in a mean size range of 0.1 to 10 microns as a core coated with an envelope of one or more membrane-forming phospholipids an at least one surfactant surrounding the drug core dispersed in a pharmaceutically acceptable carrier for delivery to the upper or lower respiratory tract wherein the amount of phospholipid coating on the drug microparticles is more than 0.1% and less than 200% of the weight of the drug.

16. A dry powder having a density in the range of from 1.0 to 1.5 g/ml consisting essentially of stabilized drug microcrystals in a mean size range of 0.1 to 10 microns as a core coated with an envelope of one or more membrane-forming phospholipids and at least one surfactant surrounding the drug core wherein the amount of phospholipid coating on the drug microparticles is more than 0.1% and less than 200% of the weight of the drug.

* * * * *